US006140483A

United States Patent [19]
Randazzo

[11] Patent Number: 6,140,483
[45] Date of Patent: Oct. 31, 2000

[54] HUMAN POLYHOMEOTIC 2 (HPH2) ACTS AS A TUMOR SUPPRESSOR

[75] Inventor: Filippo Randazzo, Emeryville, Calif.

[73] Assignee: Chiron Corporation, Emeryville, Calif.

[21] Appl. No.: 08/974,380

[22] Filed: Nov. 19, 1997

Related U.S. Application Data

[60] Provisional application No. 60/031,396, Nov. 19, 1996.

[51] Int. Cl.[7] .................................................. C07H 21/02
[52] U.S. Cl. .................... 536/23.1; 536/23.5; 530/387.1; 530/387.9; 530/388.1; 530/388.8; 530/388.85; 530/389.1; 530/389.7
[58] Field of Search ................................. 536/23.1, 23.5; 530/350, 387.1, 387.9, 388.1, 388.8, 388.85, 389.1, 389.7

[56] References Cited

FOREIGN PATENT DOCUMENTS

WO 98/07858  2/1998  WIPO .
WO 98/07860  2/1998  WIPO .

OTHER PUBLICATIONS

Database Genbank, Accession No. U89278, Mar. 1997.
Database Genbank, Accession No. S73882, Mar. 1995.
Database Genbank, Accession No. N72124, Mar. 1996.
Database Genbank, Accession No. H43989, Mar. 1995.
Campbell, Monoclonal Antibody Technology, Elsevier Science Publ. p. 1–33, 1986.
Sato et al., "Homoeosis in Drosophila: A New Enhancer of Polycomb and Related Homoeotic Mutations" *Genetics* 105:357–370, Oct. 1983.
Kennison and Tamkun, "Dosage–Dependent Modifiers of Polycomb and Antennapedia Mutations in Drosophila" *Proc. Natl. Acad. Sci. USA* 85:8136–8140, Nov. 1988.
Lewin, "Commitment and Activation at Pol II Promoters: A Tail of Protein–Protein Interactions" *Cell* 61:1161–1164, Jun., 1990.
Paro, "Imprinting a Determined State into the Chromatin of Drosophila" *TIG* 6(20) :416–421, Dec., 1990.
Goebl, "The bmi–1 and mel–18 Gene Products Define a New Family of DNA–Binding Proteins Involved in Cell Proliferation and Tumorigenesis" *Cell* 66:623, Aug., 1991.
Brunk et al., "Drosophila Genes Posterior Sex Combs and Suppressor Two of Zeste Encode Proteins With Homology to the Murine bmi–1 Oncogene" *Nature* 353:351–353, Sep., 1991.
van Lohuizen et al., "Sequence Similarity Between the Mammalian bmi–1 Proto–Oncogene and the *Drosophila* Regulatory Genes Psc and Su(z)2" *Nature* 353:353–355, Sep., 1991.
DeCamillis et al., "The Polyhomeotic Gene of Drosophila Encodes a Chromatin Protein that Shares Polytene Chromosome–Binding Sites with Polycomb" *Genes and Development* 6:223–232, 1992.
Felsenfeld, "Chromatin as an Essential Part of the Transcriptional Mechanism" *Nature* 355:219–224, Jan., 1992.
Sinclair et al., "Genetic Analysis of the Additional Sex Combs Locus of *Drosophila Melanogaster*" *Genetics* 130:817–825, Apr., 1992.
Travers, "The Reprogramming of Transcriptional Competence" *Cell* 69:573–575, May, 1992.
Djabali et al., "A Trithorax–Like Gene is Interrupted by Chromosome 11q23 Translocations in Acute Leukamias" *Nature Genetics* 2:113–118, Oct., 1992.

(List continued on next page.)

*Primary Examiner*—Sheela Huff
*Attorney, Agent, or Firm*—Jane E. R. Potter; Kimberlin L. Morley; Robert P. Blackburn

[57] ABSTRACT

A human tumor suppressor gene termed polyhomeotic 2 and its expression products can be used as therapeutic, prognostic, and diagnostic tools for proliferative and developmental disorders. Nucleotide sequences of the gene can also be used to identify a p34.3 region of a human chromosome 1.

20 Claims, 1 Drawing Sheet

OTHER PUBLICATIONS

Gu et al., "The t(4;11) Chromosome Translocation of Human Acute Leukemias Fuses the All–1 Gene, Related to Drosophila trithorax, to the AF–4 Gene" *Cell* 71:701–708, Nov., 1992.

Tkachuk et al., "Involvement of a Homolog of Drosophila Trithorax by 11q23 Chromosomal Translocations in Acute Leukemias" *Cell* 71:691–700, Nov., 1992.

Winston and Carlson, "Yeast SNF/SWI Transcriptional Activators and the SPT/SIN Chromatin Connection" *TIG* 8(11) : 387–391, Nov., 1992.

Barba et al., "Hox Gene Expression in Human Cancers" *Advances in Nutrition and Cancer*, Zappia et al., Eds., Plenum Press, N.Y., pp. 45–57, 1993.

Cillo, "Hox Genes in Human Cancers" *Invasion Metastasis* 14:38–49, 1994–1995.

Moehrle and Paro, "Spreading the Silence: Epigenetic Transcriptional Regulation During Drosophila Development" *Developmental Genetics* 15:478–484, 1994.

Kennison, "Transcriptional Activation of Drosophila Homeotic Genes from Distant Regulatory Elements" *TIG* 9(3):75–79, Mar., 1993.

van der Lugt et al., "Posterior Transformation, Neurological Abnormalities, and Severe Hematopoietic Defects in Mice with a Targeted Deletion of the bmi–1 proto–oncogene" *Genes and Development* 8: 757–769, 1994.

Denis and Green, "A Novel, Mitogen–Activated Nuclear Kinase is Related to a *Drosophila* Developmental Regulator" *Genes and Development* 10:261–271, 1996.

Epstein, "Polycomb and Friends" *BioEssays* 14(6) : 411–413, 1992.

Chiba et al., "Two Human Homologues of *Saccharomcyces cerevisiae* SW12/SNF2 and *Drosophila brahma* are Transcriptional Coactivators Cooperating with the Estrogen Receptor and the Retionic Acid Receptor" *Nucleic Acids Research* 22(10):1815–1820, 1994.

Nomura et al., "Isolation and Characterization of Retionic Acid–Inducible cDNA Clones in F9 Cells: One of the Early Inducible Clones Encodes a Novel Protein Sharing Several Highly Homologous Regions with a *Drosophila polyhomeotic* Protein" *Differentiation* 57:39–50, 1994.

Watson et al., "*Drosophila* in Cancer Research: the First Fifty Tumor Suppressor Genes" *J. Cell Science* 18:19–33, 1994.

Kanno et al., "mel–18, a Polycomb Group–Related Mammalian Gene, Encodes a Transcriptional Negative Regulator With Tumor Suppressive Activity" *The EMBO Journal* 14(22) :5672–5678, 1995.

Santamaria and Randsholt, "Characterization of a Region of the X Chromosome of *Drosophila* Including *multi sex combs* (mxc), a *Polycomb* Group Gene which also Functions as a Tumour Suppressor" *Mol. Gen. Genet.* 246:282–290, 1995.

Pirrotta, "Chromatin Complexes Regulating Gene Expression in *Drosophila*" *Current Opinion in Genetics and Development* 5:466–472, 1995.

Stuart et al., "PAX and HOX in Neoplasia" *Advances in Genetics* 33:255–274, 1995.

Tamkun, "The Role of Brahma and Related Proteins in Transcription and Development" *Current Opinion in Genetics and Development* 5:473–477, 1995.

Yu et al., "Altered Hox Expression and Segmental Indentity in *Mll*–mutant Mice" *Nature* 378:505–508, Nov., 1995.

Gunster et al., "Identification and Characterization of Interactions Between the Vertebrate Polycomb–Group Protein BMI1 and Human Homologs of Polyhomeotic" *Molecular and Cellular Biology* 17(4) :2326–2335, Apr., 1997.

Hillier et al., "yv49g08.sl Soares Fetal Liver Spleen 1NFLS Homo Sapiens cDNA clone 2461103'", Feb. 21, 1996, Database EMBL—EMEST7 Entry HS577293, Acc. No. N55577, (XP002061301).

Gunster et al., "Human Polyhomeotic 2 Homolog (HPH2) mRNA, Complete cds.", Mar. 17, 1997, Database EMBL—EMHUM2 Entry HSU89278, Acc. No. U89278 (XP002061600).

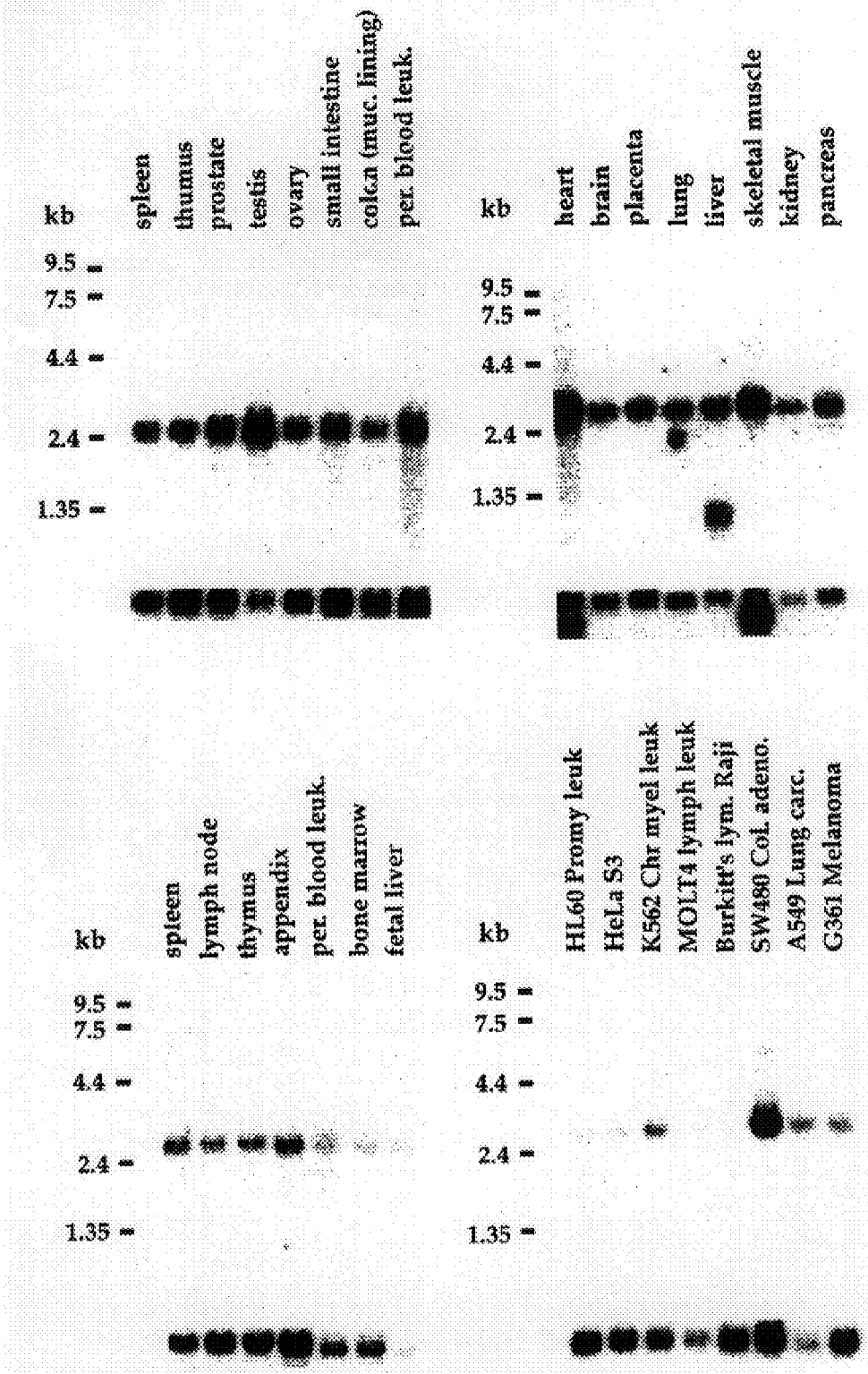

HUMAN POLYHOMEOTIC 2 (HPH2) ACTS AS A TUMOR SUPPRESSOR

This application claims the benefit of copending provisional application Ser. No. 60/031,396, filed Nov. 19, 1996, which is incorporated by reference herein.

TECHNICAL AREA OF THE INVENTION

The invention relates to the area of tumor suppression. More particularly, the invention relates to tumor suppressor genes and proteins.

BACKGROUND OF THE INVENTION

Mutations in tumor suppressor genes play an important role in the development of neoplasias. Manipulation of tumor suppressor gene expression can be used to prevent or treat neoplasias. Detection of mutations in tumor suppressor genes can also be used to detect neoplastic cells and genetic predispositions to neoplasias. Thus, there is a need in the art for the identification of mammalian tumor suppressor genes which can be used in methods of diagnosing, prognosing, and treating neoplastic cells in humans and other mammals.

SUMMARY OF THE INVENTION

It is an object of the invention to provide an isolated and purified human polyhomeotic 2 protein.

It is another object of the invention to provide an isolated and purified human polyhomeotic 2 polypeptide.

It is yet another object of the invention to provide an hph2 fusion protein.

It is still another object of the invention to provide a preparation of antibodies which specifically bind to a human polyhomeotic 2 protein.

It is yet another object of the invention to provide an isolated and purified subgenomic polynucleotide.

It is still another object of the invention to provide an expression construct for expressing all or a portion of a human polyhomeotic 2 protein.

It is a further object of the invention to provide a homologously recombinant cell comprising a DNA construct.

It is even another object of the invention to provide a method of identifying neoplastic tissue of a human.

It is another object of the invention to provide a method to aid in the diagnosis or prognosis of neoplasia in a human.

It is yet another object of the invention to provide a method to aid in detecting a genetic predisposition to neoplasia in a human.

It is still another object of the invention to provide a method of identifying a human chromosome 1.

It is even another object of the invention to provide a therapeutic composition for restoring a wild-type human polyhomeotic 2 function to a cell which lacks that function.

It is another object of the invention to provide a method of treating proliferative disorders.

It is still another object of the invention to provide a method of inducing a cell to differentiate.

These and other objects of the invention are provided by one or more of the embodiments described below.

One embodiment of the invention provides an isolated and purified human polyhomeotic 2 protein. The isolated and purified human polyhomeotic 2 protein has the amino acid sequence shown in SEQ ID NO:2.

Another embodiment of the invention provides an isolated and purified human polyhomeotic 2 protein. The isolated and purified human polyhomeotic 2 protein has an amino acid sequence which is at least 85% identical to the amino acid sequence shown in SEQ ID NO:2.

Even another embodiment of the invention provides an isolated and purified human polyhomeotic 2 polypeptide. The isolated and purified human polyhomeotic 2 polypeptide consists of at least 14 contiguous amino acids selected from the amino acid sequence shown in SEQ ID NO:2.

Yet another embodiment of the invention provides a human polyhomeotic 2 fusion protein. The human polyhomeotic 2 fusion protein comprises a first protein segment and a second protein segment fused together by means of a peptide bond. The first protein segment consists of at least 14 contiguous amino acids of a human polyhomeotic 2 protein.

Still another embodiment of the invention provides a preparation of antibodies which specifically bind to a human polyhomeotic 2 protein.

Even another embodiment of the invention provides an isolated and purified subgenomic polynucleotide. The isolated and purified subgenomic polynucleotide consists of at least 11 contiguous nucleotides selected from the nucleotide sequence shown in SEQ ID NO:1.

Yet another embodiment of the invention provides an expression construct for expressing all or a portion of a human polyhomeotic 2 protein. The expression construct comprises a promoter and a polynucleotide segment. The polynucleotide segment encodes at least 14 contiguous amino acids of a human polyhomeotic 2 protein. The polynucleotide segment is located downstream from the promoter. Transcription of the polynucleotide segment initiates at the promoter.

A further embodiment of the invention provides a homologously recombinant cell. The homologously recombinant cell comprises an incorporated new transcription unit wherein the new transcription unit comprises an exogenous regulatory sequence, an exogenous exon, and a splice donor site. The transcription unit is located upstream of a coding sequence of an hph2 gene. The exogenous regulatory sequence directs transcription of the coding sequence of the hph2 gene. The new transcription unit is incorporated into the genome using segments of homologous DNA from the hph2 gene.

Still another embodiment of the invention provides a method of identifying neoplastic tissue of a human. The method comprises comparing the expression of a polyhomeotic 2 gene in a first tissue of a human suspected of being neoplastic with the expression of a polyhomeotic 2 gene in a second tissue of the human which is normal. Underexpression of the human polyhomeotic 2 gene in the first tissue identifies the first tissue as being neoplastic.

Even another embodiment of the invention provides a method to aid in the diagnosis or prognosis of neoplasia in a human. The method comprises comparing a polyhomeotic 2 gene, mRNA, or protein in a first tissue of a human suspected of being neoplastic with a polyhomeotic 2 gene, mRNA, or protein in a second tissue of a human which is normal. A difference between the polyhomeotic 2 genes, mRNAs, or proteins in the first and second tissues indicates neoplasia in the first tissue.

Another embodiment of the invention provides a method to aid in detecting a genetic predisposition to neoplasia in a human. The method comprises comparing a polyhomeotic 2 gene, mRNA, or protein in a fetal tissue of a human with a wild-type human polyhomeotic 2 gene, mRNA, or protein. A difference between the polyhomeotic 2 gene, mRNA, or protein in the fetal tissue of the human and the wild-type human polyhomeotic 2 gene, mRNA, or protein indicates a genetic predisposition to neoplasia in the human.

Yet another embodiment of the invention provides method of identifying a human chromosome 1. The method comprises the steps of contacting a preparation of metaphase human chromosomes with a nucleotide probe comprising at least 12 contiguous nucleotides selected from the nucleotide sequence shown in SEQ ID NO:1 and detecting a region of a chromosome which specifically hybridizes to the nucleotide probe. A region of a chromosome which specifically hybridizes to the nucleotide probe is identified as a region of human chromosome 1.

Even another embodiment of the invention provides a therapeutic composition for restoring a wild-type human polyhomeotic 2 function to a cell which lacks that function. The therapeutic composition comprises all or a portion of a wild-type human polyhomeotic 2 gene or expression product and a pharmaceutically acceptable carrier. Said all or a portion of the wild-type human polyhomeotic 2 gene or expression product is capable of restoring a wild-type polyhomeotic 2 function to a cell.

Still another embodiment of the invention provides a method of treating proliferative disorders. The method comprises the step of administering to a human a composition comprising all or a portion of a wild-type human polyhomeotic 2 gene or expression product. Said all or a portion of the wild-type human polyhomeotic 2 gene or expression product is capable of restoring or enhancing a wild-type polyhomeotic 2 function to a cell.

A further embodiment of the invention provides a method of inducing a cell to change its pattern of differentiation. The method comprises the step of contacting a cell with an effective amount of a composition comprising all or a portion of a human polyhomeotic 2 gene or expression product. Said all or a portion of the human polyhomeotic 2 gene or expression product is capable of inducing the cell to change its pattern of differentiation.

The present invention thus provides the art with a novel human tumor suppressor gene called polyhomeotic 2 (hph2). The hph2 gene and protein can be used, inter alia, as therapeutic, prognostic, and diagnostic tools for proliferative and developmental disorders and to identify a p34.3 region of a human chromosome 1.

BRIEF DESCRIPTION OF THE DRAWINGS

FIG. 1. Northern blots probed with an hph2 nucleotide probe. The FIGURE depicts hph2 mRNA expression in human tissues and cancer cell lines.

DETAILED DESCRIPTION OF THE PREFERRED EMBODIMENTS

It is a discovery of the present invention that human polyhomeotic 2 functions as a tumor suppressor and thus is implicated in neoplasias and other proliferative disorders, such as dysplasias and hyperplasias. The human polyhomeotic 2 gene, protein, and mRNA can be used as a diagnostic, prognostic, and therapeutic tool for these disorders. Coding sequences of hph2 can also be used to identify a human chromosome 1.

The coding region of the hph2 gene has the nucleotide sequence shown in SEQ ID NO:1. Degenerate sequences encoding the same amino acid sequence of human polyhomeotic 2 protein or hph2 variants (see below), as well as homologous nucleotide sequences which vary by up to 5, 10, 15, 20, 25, or 30%, are included herein. Typically, homologous sequences can be confirmed by hybridization under stringent conditions (see below).

The hph2 gene maps to human chromosome 1p34.3, a region known for loss of heterozygosity in colon and gastric cancer. While not wanting to be bound by any particular theory, it is believed that there are lethal alleles of hph2 which are involved in neoplasias, such as leukemias, colon carcinoma, lung carcinoma, and melanoma. In addition, it is believed that hph2 is involved in dyplastic disorders, such as cervical epithelial dysplasia, and hyperplastic disorders, such as breast, prostate, or thyroid hyperplasias.

Human polyhomeotic 2 mRNA comprises a 3.1 kb transcript. Northern blots of human polyA$^+$ RNA probed with an hph2 nucleotide probe demonstrate that the 3.1 kb transcript is expressed, inter alia, in adult spleen, thymus, prostate, testis, ovary, small intestine, mucosal lining of the colon, peripheral blood leukocytes, heart, brain, placenta, lung, liver, skeletal muscle, kidney, pancreas, peripheral blood leukocytes, bone marrow, and appendix (FIG. 1). The 3.1 kb transcript is also expressed at low levels in fetal liver and at relatively low levels in the human cancer cell lines HL60, HeLa S3, K562, MOLT4, Burkitt's lymphoma Raji, A549, and G361. The transcript is expressed at relatively higher levels in the SW480 cell line.

Human polyhomeotic 2 protein has the amino acid sequence shown in SEQ ID NO:2. Any naturally occurring variants of this sequence which may occur in human tissues and which have, for example, tumor suppressive or antiproliferative activity, are within the scope of this invention.

Nonnaturally occurring polyhomeotic 2 variants which differ by as much as, for example, four amino acids and retain substantially the same biological activities as naturally occurring polyhomeotic 2 variants are also included here. The nonnaturally occurring polyhomeotic 2 variants have substantially the same amino acid sequences. That is, the molecules preferably are at least 85%, 90%, or 95% identical and have similar biological properties. More preferably, the molecules are 98% identical. A protein which is derived from a polyhomeotic 2 molecule has the same or substantially the same amino acid sequence as a region of the polyhomeotic 2 molecule. It can be either glycosylated or unglycosylated.

Preferably the amino acid changes in polyhomeotic 2 variants or derivatives are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids. It is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule, especially if the replacement does not involve an amino acid at a binding site involved in an interaction of polyhomeotic 2 protein. Whether an amino acid change results in a functional polyhomeotic 2 protein or polypeptide can readily be determined by assaying the tumor suppressive properties of the protein or polypeptide, as described below.

Variants of hph2 proteins have substantially the same biological activities, that is, for example, tumor suppressive activities which are of the same type as an hph2 protein having the amino acid sequence shown in SEQ ID NO:2, although the activities may differ in degree. Human polyhomeotic 2 polypeptide derivatives differ in length from natural hph2 polypeptides and contain five or more amino acids from hph2 in the same primary order as found in hph2 as obtained from a natural source. Polypeptide molecules having substantially the same amino acid sequence as hph2 but possessing minor amino acid substitutions which do not substantially affect the ability of the hph2 polypeptide derivatives to interact with hph2-specific molecules, such as antibodies, are within the definition of hph2. Derivatives include glycosylated forms, aggregative conjugates with other molecules, and covalent conjugates with unrelated chemical moieties. Derivatives also include allelic variants, species variants, and muteins. Truncations or deletions of regions which do not affect biological function are also variants or derivatives of hph2. Covalent derivatives can be prepared by linkage of functionalities to groups which are found in the amino acid chain or at the N- or C-terminal residue, as is known in the art.

Human polyhomeotic 2-specific molecules include polypeptides such as antibodies, which are specific for an hph2 polypeptide containing a naturally occurring hph2 amino acid sequence. Human polyhomeotic 2-specific binding polypeptides bind to hph2 and its derivatives and have a measurably higher binding affinity for an hph2 polypeptide or polypeptide derivative than for non-hph2 polypeptides. Higher affinity by a factor of 10 is preferred, more preferably by a factor of 100.

Human polyhomeotic 2 polypeptides preferably comprise at least 14, 15, 18, 20, 25, 30, or 35 contiguous amino acids of the amino acid sequence shown in SEQ ID NO:2. Both full-length human polyhomeotic 2 protein and polypeptides are useful for generating antibodies against human polyhomeotic 2 amino acid sequences. Human polyhomeotic 2 proteins and polypeptides can be isolated and purified from human cells such as adult spleen, thymus, prostate, testis, ovary, small intestine, mucosal lining of the colon, peripheral blood leukocytes, heart, brain, placenta, lung, liver, skeletal muscle, kidney, pancreas, peripheral blood leukocytes, bone marrow, and appendix.

Polyhomeotic 2 proteins or polypeptides can be purified by any method known in the art. These methods include, but are not limited to, size exclusion chromatography, ammonium sulfate fractionation, ion exchange chromatography, affinity chromatography, crystallization, electrofocusing, immunoprecipitation, immunoaffinity chromatography, and preparative gel electrophoresis. The skilled artisan can readily select methods which will result in a preparation of hph2 protein or polypeptide which is substantially free from other proteins and from carbohydrates, lipids, or subcellular organelles. A preparation of isolated and purified hph2 protein is at least 80% pure; preferably, the preparations are 90%, 95%, or 99% pure. Purity of the preparations may be assessed by any means known in the art, such as SDS-polyacrylamide gel electrophoresis.

Polyhomeotic 2 proteins and polypeptides can also be produced by recombinant DNA methods or by synthetic chemical methods. For production of recombinant hph2 proteins or polypeptides, coding sequences selected from the nucleotide sequence shown in SEQ ID NO:1 can be expressed in known prokaryotic or eukaryotic expression systems. Bacterial, yeast, insect, or mammalian expression systems can be used, as is known in the art. Alternatively, synthetic chemical methods, such as solid phase peptide synthesis, can be used to synthesize hph2 protein or polypeptides.

Fusion proteins containing at least fourteen contiguous hph2 amino acids can also be constructed. Human polyhomeotic 2 fusion proteins are useful for generating antibodies against hph2 amino acid sequences and for use in various assay systems. For example, hph2 fusion proteins can be used to identify proteins which interact with hph2 protein and influence its function. Physical methods, such as protein affinity chromatography, or library-based assays for protein-protein interactions, such as the yeast two-hybrid or phage display systems, can be used for this purpose. Such methods are well known in the art and can be used, inter alia, as drug screens.

An hph2 fusion protein comprises two protein segments fused together by means of a peptide bond. The first protein segment comprises at least 8, 10, 12, 15, or 20 contiguous amino acids of an hph2 protein. The amino acids can be selected from the amino acid sequence shown in SEQ ID NO:2 or from a naturally or nonnaturally occurring biologically active variant of that sequence, such as those described above. The first protein segment can also be a full-length hph2 protein. The second protein segment can be a full-length protein or a protein fragment or polypeptide. The fusion protein can be labeled with a detectable marker, as is known in the art, such as a radioactive, fluorescent, chemiluminescent, or biotinylated marker. The second protein segment can be an enzyme which will generate a detectable product, such as β-galactosidase or other enzymes which are known in the art. The first protein segment may be N-terminal or C-terminal, as is convenient.

Techniques for making fusion proteins, either recombinantly or by covalently linking two protein segments, are also well known. Recombinant DNA methods can be used to construct hph2 fusion proteins, for example, by making a DNA construct which comprises coding sequences selected from SEQ ID NO:1 in proper reading frame with nucleotides encoding the second protein segment and expressing the DNA construct in a host cell, as described below.

Isolated and purified hph2 proteins, polypeptides, or fusion proteins can be used as immunogens, to obtain a preparation of antibodies which specifically bind to an hph2 protein. The antibodies can be used to detect wild-type hph2 proteins in human tissue and fractions thereof. The antibodies can also be used to detect the presence of mutations in the hph2 gene which result in underexpression of the hph2 protein or in expression of hph2 proteins with altered size or electrophoretic mobilities.

Preparations of polyclonal and monoclonal hph2 antibodies can be made using standard methods known in the art. The antibodies specifically bind to epitopes present in hph2 proteins having the amino acid sequence shown in SEQ ID NO:2 or in naturally or non-naturally occurring variants of that sequence. Preferably, the hph2 epitopes are not present in other human proteins. Typically, at least 6, 8, 10, or 12 contiguous amino acids are required to form an epitope. However, epitopes which involve non-contiguous amino acids may require more, e.g., at least 15, 25, or 50 amino acids. Antibodies which specifically bind to hph2 proteins provide a detection signal at least 5-, 10-, or 20-fold higher than a detection signal provided with other proteins when used in Western blots or other immunochemical assays. Preferably, antibodies which specifically bind hph2 proteins do not detect other proteins in immunochemical assays and can immunoprecipitate hph2 proteins from solution.

Human polyhomeotic 2 antibodies can be purified by methods well known in the art. Preferably, the antibodies are affinity purified, by passing antiserum over a column to which an hph2 protein, polypeptide, or fusion protein is bound. The bound antibodies can then be eluted from the column, for example, using a buffer with a high salt concentration.

Purified and isolated hph2 subgenomic polynucleotides can be used, inter alia, as primers to obtain additional copies of the polynucleotides, to express human polyhomeotic 2 mRNA, protein, polypeptides, or fusion proteins, and as probes for identifying wild-type and mutant hph2 coding sequences. The probes can also be used to identify the short arm of a human chromosome 1, as described below.

Purified and isolated hph2 subgenomic polynucleotides of the invention comprise at least 11, 13, 15, 18, 20, 25, or 30 contiguous nucleotides selected from SEQ ID NO:1. Subgenomic hph2 polynucleotides according to the invention contain less than a whole chromosome. Preferably, the polynucleotides are intron-free.

Subgenomic hph2 polynucleotides can be isolated and purified free from other nucleotide sequences using standard nucleic acid purification techniques. For example, restriction enzymes and probes can be used to isolate polynucleotide fragments which comprise hph2 coding sequences. Isolated polynucleotides are in preparations which are free or at least 90% free of other molecules.

Degenerate or homologous sequences which encode hph2 protein are also included herein. Two nucleic acid fragments are homologous if they are capable of hybridizing to one another under hybridization conditions described in Sambrook et al., MOLECULAR CLONING: A LABORATORY MANUAL, 2d ed. (Cold Spring Harbor Press, Cold Spring Harbor, N.Y.). Using the following wash conditions—2× SCC, 0.1% SDS, room temperature twice, 30 minutes each; then 2×SCC, 0.1% SDS, 50° C. once for 30 minutes; then 2×SCC, room temperature twice, 10 minutes each—homologous sequences can be identified that contain at most about 25–30% basepair mismatches. More preferably, homologous nucleic acid strands contain 15–25% basepair mismatches, even more preferably 5–15% basepair mismatches. These degrees of homology can be selected by using more stringent wash conditions for identification of clones from gene libraries (or other sources of genetic material), as is well known in the art.

DNA fragments derived from an hph2-encoding DNA sequence are also included herein. A DNA fragment derived from an hph2 coding sequence has the same or substantially the same basepair sequence as a region of the coding sequence of the entire hph2 molecule. Preferably the DNA fragment has at least 95% or preferably at least 98% or at least 99% identity with hph2.

Complementary DNA encoding hph2 proteins can be made using reverse transcriptase, with hph2 mRNA as a template. The polymerase chain reaction (PCR) can be used to obtain hph2 polynucleotides, using either human genomic DNA or cDNA as a template. Alternatively, synthetic chemistry techniques can be used to synthesize polynucleotide molecules of the invention. The degeneracy of the genetic code allows alternate nucleotide sequences to be synthesized which will encode a polyhomeotic 2 protein having the amino acid sequence shown in SEQ ID NO:2. All such nucleotide sequences are within the scope of the present invention.

An hph2 subgenomic polynucleotide of the present invention can be used in an expression construct, to express all or a portion of an hph2 protein in a host cell. The host cell comprising the expression construct can be prokaryotic or eukaryotic. A variety of host cells for use in bacterial, yeast, insect, and human expression systems are available and can be used to express the expression construct. The expression constructs can be introduced into the host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, and calcium phosphate-mediated transfection.

The expression construct comprises a promoter which is functional in the particular host cell selected. The skilled artisan can readily select an appropriate promoter from the large number of cell type-specific promoters known and used in the art. The expression construct can also contain a transcription terminator which is functional in the host cell. The expression construct comprises a polynucleotide segment which encodes all or a portion of an hph2 protein. The polynucleotide segment is located downstream from the promoter. Transcription of the polynucleotide segment initiates at the promoter. The expression construct can be linear or circular and can contain sequences, if desired, for autonomous replication.

The hph2 gene maps to human chromosome region 1p34.3. Thus, the subgenomic polynucleotides of the invention can be used to identify this chromosome region in metaphase spreads of human chromosomes. Preparations of human metaphase chromosomes can be prepared using standard cytogenetic techniques from human primary tissues or cell lines. Nucleotide probes comprising at least 12 contiguous nucleotides selected from the nucleotide sequence shown in SEQ ID NO:1 are used to identify the human chromosome. The nucleotide probes can be labeled, for example, with a radioactive, fluorescent, biotinylated, or chemiluminescent label, and detected by well known methods appropriate for the particular label selected. Protocols for hybridizing nucleotide probes to preparations of metaphase chromosomes are well known in the art. A nucleotide probe will hybridize specifically to nucleotide sequences in the chromosome preparations which are complementary to the nucleotide sequence of the probe. A probe which hybridizes specifically to human chromosome region 1p34.3 hybridizes to nucleotide sequences present in the hph2 gene and not to nucleotide sequences present in other human genes. A probe which hybridizes specifically to an hph2 gene provides a detection signal at least 5-, 10-, or 20-fold higher than the background hybridization provided with non-hph2 coding sequences.

A human chromosome which specifically hybridizes to an hph2 nucleotide probe is identified as a human chromosome 1. Preferably, the nucleotide probe identifies the short arm of human chromosome 1. More preferably, the nucleotide probe identifies a p34.3 region of human chromosome 1.

The present invention also provides a method to identify neoplastic tissue in a human. The expression of an hph2 gene can be compared between a first tissue which is suspected of being neoplastic and a second tissue of the human which is normal. The normal tissue can be any tissue of the human, especially those which express the hph2 gene, including, but not limited to, adult spleen, thymus, prostate, testis, ovary, small intestine, mucosal lining of the colon, peripheral blood leukocytes, heart, brain, placenta, lung, liver, skeletal muscle, kidney, pancreas, peripheral blood leukocytes, bone marrow, and appendix. The tissue suspected of being neoplastic can be derived from a different tissue type of the human, but preferably it is derived from the same tissue type, for example an intestinal polyp or other abnormal growth. Without being limited to any particular theory, the inventor believes that a difference between the hph2 gene (or a gene which regulates, for example, its expression, half-life, or degradation), mRNA, or protein in the two tissues which are compared indicates a somatic mutation in the hph2 gene in the tissue of the human which was suspected of being neoplastic. Such differences can be, for example, differences in molecular weight, amino acid or nucleotide sequence, or relative abundance.

The hph2 genes in the two tissues can be compared by any means known in the art. For example, the two genes can be sequenced, and the sequence of the hph2 gene in the tissue suspected of being neoplastic can be compared with the wild-type hph2 sequence in the normal tissue. The hph2 genes or portions of the hph2 genes in the two tissues can be amplified, for example, using nucleotide primers selected from the nucleotide sequence shown in SEQ ID NO:1 in the polymerase chain reaction (PCR). The amplified genes or portions of genes can be hybridized to nucleotide probes selected from the nucleotide sequence shown in SEQ ID NO:1. The nucleotide probes can be labeled by a variety of methods, such as radiolabeling, biotinylation, or coupling to fluorescent or chemiluminescent tags, and detected by standard methods known in the art.

Alternatively, hph2 mRNA in the two tissues can be compared. PolyA$^+$ RNA can be isolated from the two tissues as is known in the art. For example, one of skill in the art can readily determine differences in the size or amount of hph2 mRNA transcripts between the two tissues that are compared, using Northern blots and nucleotide probes selected from the nucleotide sequence shown in SEQ ID NO:1. Underexpression of hph2 mRNA in a tissue sample suspected of being neoplastic compared with the expression of hph2 mRNA in a normal tissue is indicative of neoplasia.

Any method for analyzing proteins can be used to compare two hph2 proteins from matched samples. The sizes of the hph2 proteins in the two tissues can be compared, for example, using antibodies of the present invention to detect hph2 proteins in Western blots of protein extracts from the two tissues. Other changes, such as expression levels and subcellular localization, can also be detected immunologically. A lower hph2 protein expression level in a tissue suspected of being neoplastic compared with the hph2 protein expression level in a normal tissue is indicative of neoplasia.

Similarly, comparison of hph2 gene sequences or of hph2 gene expression products, e.g., mRNA and protein, between a tissue of a human which is suspected of being neoplastic and a normal tissue of a human can be used to diagnose or prognose neoplasia in the human. Such comparisons of hph2 genes, mRNA, or protein can be made as described above. Underexpression of the hph2 gene in the tissue suspected of being neoplastic indicates neoplasia in the tissue. The degree of underexpression of the hph2 gene in the neoplastic tissue relative to wild-type expression of the gene in normal tissue, or differences in the amount of underexpression of the hph2 gene in the neoplastic tissue over time, can be used to prognose the progression of the neoplasia in that tissue or to monitor the response of the neoplastic tissue to various therapeutic regimens.

A genetic predisposition to neoplasia in a human can be detected by comparing a wild-type hph2 gene, mRNA, or protein with an hph2 gene, mRNA, or protein in a fetal tissue. Fetal tissues which can be used for this purpose include, but are not limited to, amniotic fluid, chorionic villi, blood, and the blastomere of an in vitro-fertilized embryo. The wild-type hph2 gene can be obtained from any tissue. The mRNA or protein can be obtained from a normal tissue of a human in which the hph2 gene is expressed. Such tissues are disclosed above. Differences, such as alterations in the nucleotide sequence or size of the fetal hph2 gene or mRNA, or alterations in the molecular weight, amino acid sequence, or relative abundance of fetal hph2 protein, indicate a germline mutation in the hph2 gene of the fetus which indicates a genetic predisposition to neoplasia.

Human polyhomeotic 2 subgenomic polynucleotides or proteins can also be used to induce differentiation of a progenitor cell, e.g., in order to study the process of differentiation and to test compounds which affect this process. Induction of differentiation is also desirable, for example, in the treatment of anaplastic tumors, which are composed of cells which have lost some of their differentiated characteristics. Progenitor cells which can be induced to differentiate using an hph2 therapeutic composition comprising hph2 subgenomic polynucleotides, proteins, polypeptides, or fusion proteins include, but are not limited to, erythropoietic stem cells, neuroblasts, chrondroblasts, melanoblasts, myoblasts, and neural crest cells. Differentiated cells can also be induced to de-differentiate.

Cells transformed with wild-type hph2 subgenomic polynucleotides can be used as model systems to study cancer remission and drug treatments which promote such remission. Suppression of the neoplastic phenotype is a process which involves alterations in gene expression in the transformed cells. These alterations in gene expression will be reflected in morphological and biochemical changes in the transformed cells. Morphological changes can be studied, for example, by observing the transformed cells microscopically and comparing the appearance of the transformed cells with cells which have not received a wild-type hph2 subgenomic polynucleotide. Biochemical alterations can be studied, inter alia, by comparing the proteins which are expressed by the cells before and at various times after transformation with the wild-type hph2 subgenomic polynucleotide. Methods of comparing proteins between two cells, such as one- or two-dimensional polyacrylamide gel electrophoresis, are well known in the art. Cells transformed with a wild-type hph2 subgenomic polynucleotide and in the process of suppressing neoplastic growth can also be exposed to various drug treatments to determine which treatments promote the morphological or biochemical changes which accompany suppression of the neoplastic phenotype. Similarly, cells transformed with wild-type hph2 subgenomic polynucleotides can also be used to study changes which accompany cellular differentiation in progenitor cells and responses of these cells to test compounds which affect differentiation. Expression of an endogenous hph2 gene in a cell can be altered by introducing in frame with the endogenous hph2 gene a DNA construct comprising an hph2 targeting sequence, a regulatory sequence, an exon, and an unpaired splice donor site by homologous recombination, such that a homologously recombinant cell comprising the DNA construct is formed. The new transcription unit can be used to turn the hph2 gene on or off as desired. This method of affecting endogenous gene expression is taught in U.S. Pat. No. 5,641,670, which is incorporated herein by reference in its entirety.

The targeting sequence is a segment of at least 10, 12, 15, 20, or 50 contiguous nucleotides selected from the nucleotide sequence shown in SEQ ID NO:1. The transcription unit is located upstream of a coding sequence of the endogenous hph2 gene. The exogenous regulatory sequence directs transcription of the coding sequence of the hph2 gene. Preferably, the homologously recombinant cell is a progenitor cell or a neoplastic cell, and the exogenous regulatory sequence directs enhanced transcription of the coding sequence of the hph2 gene.

The invention provides a therapeutic composition for restoring a wild-type. hph2 function to a cell which has lost that function. Wild-type hph2 functions include suppression of neoplasia and of dysplastic or hyperplastic cell growth, as well as the ability to induce cellular differentiation. The cell can be any cell of a human which would normally express the wild-type hph2 gene, such as adult spleen, thymus, prostate, testis, ovary, small intestine, mucosal lining of the colon, peripheral blood leukocytes, heart, brain, placenta, lung, liver, skeletal muscle, kidney, pancreas, peripheral blood leukocytes, bone marrow, and appendix, but which lacks hph2 expression or expresses an altered form of hph2 mRNA or protein. Such cells include neoplasias of the tissues mentioned above as well as any other neoplastic cells which have lost wild-type polyhomeotic 2 function. The therapeutic composition comprises all or a portion of a wild-type human hph2 gene or gene expression product in a pharmaceutically acceptable carrier. The hph2 expression product can be, e.g., mRNA or protein. A portion of a wild-type hph2 gene, mRNA, or protein can also be used if it is capable of restoring wild-type hph2 function to the cell.

Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for the therapeutic polyhomeotic 2 composition.

Typically, the therapeutic hph2 composition is prepared as an injectable, either as a liquid solution or suspension; however, solid forms suitable for solution in, or suspension in, liquid vehicles prior to injection can also be prepared. The composition can also be formulated into an enteric coated tablet or gel capsule according to known methods in the art, such as those described in U.S. Pat. No. 4,853,230, EP 225,189, AU 9,224,296, and AU 9,230,801.

Proliferative disorders, such as neoplasias, dysplasias, and hyperplasias, can be treated by administration of the therapeutic hph2 composition. Neoplasias which can be treated with the therapeutic composition include, but are not limited to, melanomas, squamous cell carcinomas, adenocarcinomas, hepatocellular carcinomas, renal cell carcinomas, sarcomas, myosarcomas, non-small cell lung carcinomas, leukemias, lymphomas, osteosarcomas, central nervous system tumors such as gliomas, astrocytomas, oligodendrogliomas, and neuroblastomas, tumors of mixed origin, such as Wilms' tumor and teratocarcinomas, and metastatic tumors. Proliferative disorders which can be treated with the therapeutic hph2 composition include disorders such as anhydric hereditary ectodermal dysplasia, congenital alveolar dysplasia, epithelial dysplasia of the cervix, fibrous dysplasia of bone, and mammary dysplasia. Hyperplasias, for example, endometrial, adrenal, breast, prostate, or thyroid hyperplasias, or pseudoepitheliomatous hyperplasia of the skin can be treated with wild-type hph2 therapeutic compositions. Even in disorders in which hph2 mutations are not implicated, increasing hph2 expression or enhancing hph2 function can have therapeutic application. In these disorders, increasing hph2 expression or enhancing hph2 function can help to suppress tumors. Similarly, in tumors where hph2 expression is not aberrant, effecting hph2 upregulation or augmentation of hph2 activity can suppress metastases.

The therapeutic composition can contain hph2 polynucleotides. Preferably, the therapeutic composition contains an expression construct comprising a promoter and a polynucleotide segment encoding at least eight contiguous amino acids of hph2 protein. Within the expression construct, the polynucleotide segment is located downstream from the promoter, and transcription of the polynucleotide segment initiates at the promoter. A more complete description of gene therapy vectors, especially retroviral vectors is contained in U.S. Ser. No. 08/869,309, which is expressly incorporated herein.

Administration of the hph2 therapeutic agents of the invention can include local or systemic administration, including injection, oral administration, particle gun, or catheterized administration, and topical administration. Various methods can be used to administer the therapeutic hph2composition directly to a specific site in the body. For example, a small metastatic lesion can be located and the therapeutic hph2 composition injected several times in several different locations within the body of tumor. Alternatively, arteries which serve a tumor can be identified, and the therapeutic composition injected into such an artery, in order to deliver the composition directly into the tumor. A tumor which has a necrotic center can be aspirated and the composition injected directly into the now empty center of the tumor. The therapeutic hph2 composition can be directly administered to the surface of the tumor, for example, by topical application of the composition. X-ray imaging can be used to assist in certain of the above delivery methods. Combination therapeutic agents, including an hph2 protein or polypeptide or a subgenomic hph2 polynucleotide and other therapeutic agents, can be administered simultaneously or sequentially.

Receptor-mediated targeted delivery of therapeutic compositions containing hph2 subgenomic polynucleotides to specific tissues can also be used. Receptor-mediated DNA delivery techniques are described in, for example, Findeis et al. (1993), Trends in Biotechnol. 11, 202–05; Chiou et al. (1994), GENE THERAPEUTICS: METHODS AND APPLICATIONS OF DIRECT GENE TRANSFER (J. A. Wolff, ed.); Wu & Wu (1988), J. Biol. Chem. 263, 621–24; Wu et al. (1994), J. Biol. Chem. 269, 542–46; Zenke et al. (1990), Proc. Natl. Acad. Sci. U.S.A. 87, 3655–59; Wu et al. (1991), J. Biol. Chem. 266, 338–42.

Alternatively, an hph2 therapeutic composition can be introduced into human cells ex vivo, and the cells then replaced into the human. Cells can be removed from a variety of locations including, for example, from a selected tumor or from an affected organ. In addition, the therapeutic composition can be inserted into non-tumorigenic cells, for example, dermal fibroblasts or peripheral blood leukocytes. If desired, particular fractions of cells such as a T cell subset or stem cells can also be specifically removed from the blood (see, for example, PCT WO 91/16116). The removed cells can then be contacted with the hph2 therapeutic composition utilizing any of the above-described techniques, followed by the return of the cells to the human, preferably to or within the vicinity of a tumor. The above-described methods can additionally comprise the steps of depleting fibroblasts or other non-contaminating tumor cells subsequent to removing tumor cells from a human, and/or the step of inactivating the cells, for example, by irradiation.

Both the dose of the hph2 composition and the means of administration can be determined based on the specific qualities of the therapeutic composition, the condition, age, and weight of the patient, the progression of the disease, and other relevant factors. If the composition contains hph2 protein or polypeptide, effective dosages of the composition are in the range of about 5 µg to about 50 µg/kg of patient body weight, about 50 µg to about 5 mg/kg, about 100 µg to about 500 µg/kg of patient body weight, and about 200 to about 250 µg/kg.

Therapeutic compositions containing hph2 subgenomic polynucleotides can be administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. Factors such as method of action and efficacy of transformation and expression are considerations that will effect the dosage required for ultimate efficacy of the hph2 subgenomic polynucleotides. Where greater expression is desired over a larger area of tissue, larger amounts of hph2 subgenomic polynucleotides or the same amounts readministered in a successive protocol of administrations, or several administrations to different adjacent or close tissue portions of for example, a tumor site, may be required to effect a positive therapeutic outcome. In all cases, routine experimentation in clinical trials will determine specific ranges for optimal therapeutic effect.

Synopsis of the Invention

1. An isolated and purified human polyhomeotic 2 protein having the amino acid sequence shown in SEQ ID NO:2.

2. An isolated and purified human polyhomeotic 2 protein having an amino acid sequence which is at least 85% identical to the amino acid sequence shown in SEQ ID NO:2.

3. The isolated and purified human polyhomeotic 2 protein of item 2 wherein the amino acid sequence is at least 90% identical to the amino acid sequence shown in SEQ ID NO:2.

4. The isolated and purified human polyhomeotic 2 protein of item 2 wherein the amino acid sequence is at least 95% identical to the amino acid sequence shown in SEQ ID NO:2.

5. An isolated and purified human polyhomeotic 2 polypeptide consisting of at least 14 contiguous amino acids selected from the amino acid sequence shown in SEQ ID NO:2.

6. A human polyhomeotic 2 fusion protein comprising a first protein segment and a second protein segment fused together by means of a peptide bond, wherein the first protein segment consists of at least 14 contiguous amino acids of a human polyhomeotic 2 protein.

7. A preparation of antibodies which specifically bind to a human polyhomeotic 2 protein.

8. The preparation of antibodies of item 7 wherein the antibodies are monoclonal.

9. The preparation of antibodies of item 7 wherein the antibodies are polyclonal.

10. An isolated and purified subgenomic polynucleotide consisting of at least 11 contiguous nucleotides selected from the nucleotide sequence shown in SEQ ID NO:1.

11. An expression construct for expressing all or a portion of a human polyhomeotic 2 protein comprising:
   a promoter; and
   a polynucleotide segment encoding at least 14 contiguous amino acids of a human polyhomeotic 2 protein, wherein the polynucleotide segment is located downstream from the promoter, wherein transcription of the polynucleotide segment initiates at the promoter.

12. A host cell comprising the expression construct of item 11.

13. A homologously recombinant cell having incorporated therein a new transcription initiation unit, wherein the new transcription inititation unit comprises:
   (a) an exogenous regulatory sequence;
   (b) an exogenous exon; and
   (c) a splice donor site, wherein the transcription initiation unit is located upstream of a coding sequence of an hph2 gene, wherein the exogenous regulatory sequence directs transcription of the coding sequence of the hph2 gene.

14. The homologously recombinant cell of item 13 wherein the exogenous regulatory sequence directs enhanced transcription of the coding sequence of the hph2 gene.

15. The homologously recombinant cell of item 13 wherein the homologously recombinant cell is a neoplastic cell.

16. The homologously recombinant cell of item 13 wherein the homologously recombinant cell is a progenitor cell.

17. A method of identifying neoplastic tissue of a human, comprising:
   comparing the expression of a polyhomeotic 2 gene in a first tissue of a human suspected of being neoplastic with the expression of a polyhomeotic 2 gene in a second tissue of the human which is normal, wherein underexpression of the human polyhomeotic 2 gene in the first tissue identifies the first tissue as being neoplastic.

18. The method of item 17 wherein the difference in the polyhomeotic 2 genes between the first and second tissues is detected by amplification of the polyhomeotic 2 genes of the first and second tissues and hybridization of the amplified genes to nucleotide probes.

19. The method of item 17 wherein polyhomeotic 2 mRNA is compared between the first and second tissues.

20. The method of item 17 wherein a human polyhomeotic 2 protein is compared between the first and second tissues.

21. A method to aid in the diagnosis or prognosis of neoplasia in a human, comprising:
   comparing a polyhomeotic 2 gene, mRNA, or protein in a first tissue of a human suspected of being neoplastic with a polyhomeotic 2 gene, mRNA, or protein in a second tissue of a human which is normal, wherein a difference between the polyhomeotic 2 genes, mRNAs, or proteins in the first and second tissues indicates neoplasia in the first tissue.

22. The method of item 21 wherein the polyhomeotic 2 genes in the first and second tissues are compared by sequencing the polyhomeotic 2 genes in the first and second tissues.

23. The method of item 21 wherein the difference in the polyhomeotic 2 genes between the first and second tissues is detected by amplification of the polyhomeotic 2 genes of the first and second tissues and hybridization of the amplified genes to nucleotide probes.

24. The method of item 21 wherein polyhomeotic mRNA is compared.

25. The method of item 21 wherein polyhomeotic protein is compared.

26. A method to aid in detecting a genetic predisposition to neoplasia in a human, comprising:
    comparing a polyhomeotic 2 gene, mRNA, or protein in a fetal tissue of a human with a wild-type human polyhomeotic 2 gene, mRNA, or protein, wherein a difference between the polyhomeotic 2 gene, mRNA, or protein in the fetal tissue of the human and the wild-type human polyhomeotic 2 gene, mRNA, or protein indicates a genetic predisposition to neoplasia in the human.

27. The method of item 26 wherein a polyhomeotic 2 mRNA is compared.

28. The method of item 26 wherein a polyhomeotic 2 gene is compared.

29. The method of item 26 wherein the difference between the polyhomeotic 2 genes is detected by amplification of the wild-type human polyhomeotic 2 gene and the human polyhomeotic 2 gene in the fetal tissue and hybridizing the amplified genes to nucleotide probes.

30. The method of item 26 wherein a human polyhomeotic 2 protein is compared.

31. A method of identifying a human chromosome 1, comprising the steps of:
    contacting a preparation of metaphase human chromosomes with a nucleotide probe comprising at least 12 contiguous nucleotides selected from the nucleotide sequence shown in SEQ ID NO:1; and
    detecting a region of a chromosome which specifically hybridizes to the nucleotide probe, wherein a region of a chromosome which specifically hybridizes to the nucleotide probe is identified as a human chromosome 1.

32. The method of item 31 wherein the region of the chromosome which specifically hybridizes to the nucleotide probe is identified as the short arm of a human chromosome 12.

33. The method of item 31 wherein the region of the chromosome which specifically hybridizes to the nucleotide probe is identified as a p34.3 region of a human chromosome 1.

34. A therapeutic composition for restoring a wild-type human polyhomeotic 2 function to a cell which lacks that function, comprising:
    all or a portion of a wild-type human polyhomeotic 2 gene or expression product, wherein said all or a portion of the wild-type human polyhomeotic 2 gene or expression product is capable of restoring a wild-type polyhomeotic 2 function to a cell; and
    a pharmaceutically acceptable carrier.

35. A method of treating proliferative disorders, comprising the step of administering to a human a composition comprising all or a portion of a wild-type human polyhomeotic 2 gene or expression product, wherein said all or a portion of the wild-type human polyhomeotic 2 gene or expression is capable of restoring or enhancing a wild-type polyhomeotic 2 function to a cell.

36. A method of inducing a cell to change its pattern of differentiation, comprising the step of:
    contacting a progenitor cell with an effective amount of a composition comprising all or a portion of a human polyhomeotic 2 gene or expression product, wherein said all or a portion of the human polyhomeotic 2 gene or expression product is capable of inducing the cell to change its pattern of differentiation.

What is claimed is:

1. A preparation of antibodies which specifically bind to a human polyhomeotic 2 (hph2) protein, wherein the antibodies do not detect other proteins in Western blots.

2. The preparation of antibodies of claim 1 wherein the antibodies are polyclonal.

3. The preparation of antibodies of claim 1 wherein the antibodies are monoclonal.

4. The preparation of antibodies of claim 1 wherein the antibodies are affinity purified.

5. An isolated and purified human polyhomeotic 2 protein having an amino acid sequence which contains no more than 35 conservative amino acid substitutions relative to the amino acid sequence shown in SEQ ID NO:2, wherein the conservative amino acid substitution is selected from the group consisting of (a) a first acidic amino acid for a second acidic amino acid, (b) a first basic amino acid for a second basic amino acid, (c) a first non-polar amino acid for a second non-polar amino acid, (d) a first uncharged polar amino acid for a second uncharged polar amino acid, and (e) a first aromatic amino acid for a second aromatic amino acid.

6. The isolated and purified human polyhomeotic 2 protein of claim 5 wherein the amino acid sequence contains no more than 23 conservative amino acid substitutions relative to the amino acid sequence shown in SEQ ID NO:2.

7. The isolated and purified human polyhomeotic 2 protein of claim 5 wherein the amino acid sequence contains no more than 12 conservative amino acid substitutions relative to the amino acid sequence shown in SEQ ID NO:2.

8. The isolated and purified human polyhomeotic 2 protein of claim 5 wherein the amino acid sequence contains no more than 5 conservative amino acid substitutions relative to the amino acid sequence shown in SEQ ID NO:2.

9. The isolated and purified human polyhomeotic 2 protein of claim 5 which has an antiproliferative activity.

10. An isolated and purified human polyhomeotic 2 protein having the amino acid sequence shown in SEQ ID NO:2.

11. An isolated and purified subgenomic polynucleotide comprising a polynucleotide segment encoding a human polyhomeotic 2 protein with the amino acid sequence shown in SEQ ID NO:2 or a human polyhomeotic 2 protein variant which differs by no more than four amino acids from the amino acid sequence shown in SEQ ID NO:2, wherein the polynucleotide segment contains at least 97 and no more than 580 basepair mismatches compared with the nucleotide sequence shown in SEQ ID NO:1.

12. The subgenomic polynucleotide of claim 11 wherein the polynucleotide segment comprises the nucleotide sequence shown in SEQ ID NO: 1.

13. The subgenomic polynucleotide of claim 11 wherein the polynucleotide segment contains no more than 483 basepair mismatches.

14. The subgenomic polynucleotide of claim 11 wherein the polynucleotide segment contains no more than 387 basepair mismatches.

15. The subgenomic polynucleotide of claim 11 wherein the polynucleotide segment contains no more than 290 basepair mismatches.

16. The subgenomic polynucleotide of claim 11 wherein the polynucleotide segment contains no more than 193 basepair mismatches.

17. The subgenomic polynucleotide of claim 11 wherein the polynucleotide segment contains no more than 97 basepair mismatches.

18. The subgenomic polynucleotide of claim 11 further comprising a promoter, wherein the polynucleotide segment is located downstream from the promoter, and wherein transcription of the polynucleotide segment initiates at the promoter.

19. A composition comprising the subgenomic polynucleotide of claim 11 and a pharmaceutically acceptable carrier.

20. The subgenomic polynucleotide of claim 11 wherein the human polyhomeotic protein or protein variant has an antiproliferative activity.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 1933 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
CATCTGCAAG AATCCAAAGA GGAGGGTGCT CCCCTCAAAC TCAAGTGTGA GCTCTGTGGC      60

CGGGTGGACT TTGCCTATAA GTTCAAGCGT TCCAAGCGCT TCTGTTCCAT GGCTTGTGCA     120

AAGAGGTACA ACGTGGGATG CACCAAACGG GTGGGACTTT TCCACTCAGA CCGGAGCAAG     180

CTGCAGAAGG CAGGAGCTGC GACCCACAAC CGCCGTCGGG CCAGCAAAGC CAGTCTGCCA     240

CCACTTACCA AGGATACCAA GAAGCAGCCA ACAGGCACTG TGCCCCTTTC GGTTACTGCT     300

GCTTTGCAGC TAACACACAG CCAGGAAGAC TCCAGCCGTT GCTCAGATAA CTCAAGCTAT     360
```

-continued

```
GAGGAACCCT TGTCACCCAT CTCAGCCAGC TCATCTACTT CCCGCCGGCG ACAAGGCCAG      420

CGGGACCTGG AGCTCCCCGA CATGCATATG CGGGACCTGG TGGGCATGGG ACACCACTTC      480

CTGCCAAGTG AGCCCACCAA GTGGAATGTA AAGACGTCT ACGAATTCAT CCGCTCTCTG       540

CCAGGCTGCC AGGAGATAGC AGAGGAATTC CGTGCCCAGG AAATCGACGG GCAAGCCCTG      600

CTGCTGCTCA AGGAGGACCA CCTGATGAGC GCCATGAACA TCAAGCTGGG GCCCGCCCTG      660

AAGATCTACG CCCGCATCAG CATGCTCAAG GACTCCTAGG GCTGGTGGCA GCCAGGATTC      720

TGGCCCAGGG CGCCTCCTCC CGACTGAGCA GAGCCAGACA GACATTCCTG AGGGGCCCAG      780

AAATGGGGCC GGTTGGAGGG CAGGGGCTCT CCCTAGGGGC ATAGCTGGTG AGGAGGTCTG      840

GGCACCTCCT CCATGGCTCT CAGGGGCCTT TCATTTCTGT GGGAGGGGCA GAGAGGTAGG      900

TGGCACAGAA GATGGGGCTT TATGCTTGTA AATATTGATA GCACTGGCTT CCTCCAAAGT      960

CCCAATACTC TAGCCCCGCT CTCTTCCCCT CTTTCTGTCC CCCATTTTCC AGGGGGTATA     1020

TGGTCAGGGC TCCCCAACCT GAGTTGGGTT ACTTCAAGGG CAGCCAGCAG GCCTGGATGG     1080

AGGCCTAGAA AGCCCTTGCC TTCCTTCCTC CCACTTCTTT CTCCAGGCCT GGTTAACTCT     1140

TCCGTTGTCA GCTTCTCCCC CTTCAGCCTG TTTCTGCAGC AGCCAGGGTT CTCCCCCCTA     1200

CACCCTCTGC AGGTGGAGAG AGAGAAGCTG GGCCCAGCCG GGCCGTGCCT GCTGGCACAG     1260

ACGCCTTAAC GCTGTGTGTA TGACTGTGTG ACTGTGTGGG AGCCTGGACT GACAGATAGG     1320

CCAAGGGCTA CTCTCTGGCA TCTCCAGGTG TTTTGTAGCA AACAGCCACT TAGTGCTTTG     1380

TCCTGGACTC CACTCAGCCT CAGGATGGGG AATAGCCAAG AATGGCAGCC TCAGCGCAGA     1440

GGCAAGGTCA GAAAGAGACG GCGCTTCAGA GTTTCCTTTC CAGACACCCC TCCCCGCACT     1500

GTGAAGTTCC CCTGACCGCC CTCCTGGTTC ACAAAGAGCA TTAAGAAAGC TGCGGTGGTC     1560

TGAGCAACAT AGCCCAAAGG GCTGAGCCTC CTGGCCTGCC TGCCCGCCCA CCCTGGGAGT     1620

CCCAGTGGTG AGGCTCAGAG AACTGCTAAG GGGAAAGAAC AGCTGGAGTT TCTGTTGATG     1680

TGAAGAAGGC AGCTCTTGGC CTCCCACTCC CACACTTCTT TGCCTATAAA TCTTCCTAGC     1740

AGCAATTTGA GCTACCTGAG GAGGAGGCAG GGCAGAAAGG GCGAGGGCCT GCCTCTGACC     1800

TGCCGTGTCC TTTGCAGGAA GGAGGTAGGC ACCTTTCTGA GCTTATTCTA TTCCCCACCC     1860

ACACCCCCAG GCAGGGTTGG AAATGAAGGA CTTTTTTAAC CTTTGTTTTG TTTTTTAAAA     1920

ATAAATCTGT AAG                                                        1933
```

(2) INFORMATION FOR SEQ ID NO:2:

(i) SEQUENCE CHARACTERISTICS:
        (A) LENGTH: 231 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Leu Gln Glu Ser Lys Glu Glu Gly Ala Pro Leu Lys Leu Lys Cys Glu
 1               5                  10                  15

Leu Cys Gly Arg Val Asp Phe Ala Tyr Lys Phe Lys Arg Ser Lys Arg
                20                  25                  30

Phe Cys Ser Met Ala Cys Ala Lys Arg Tyr Asn Val Gly Cys Thr Lys
            35                  40                  45

Arg Val Gly Leu Phe His Ser Asp Arg Ser Lys Leu Gln Lys Ala Gly
        50                  55                  60
```

-continued

```
Ala Ala Thr His Asn Arg Arg Ala Ser Lys Ala Ser Leu Pro Pro
 65              70              75              80

Leu Thr Lys Asp Thr Lys Lys Gln Pro Thr Gly Thr Val Pro Leu Ser
             85              90              95

Val Thr Ala Ala Leu Gln Leu Thr His Ser Gln Glu Asp Ser Ser Arg
            100             105             110

Cys Ser Asp Asn Ser Ser Tyr Glu Glu Pro Leu Ser Pro Ile Ser Ala
            115             120             125

Ser Ser Ser Thr Ser Arg Arg Arg Gln Gly Gln Arg Asp Leu Glu Leu
            130             135             140

Pro Asp Met His Met Arg Asp Leu Val Gly Met Gly His His Phe Leu
145             150             155             160

Pro Ser Glu Pro Thr Lys Trp Asn Val Glu Asp Val Tyr Glu Phe Ile
                165             170             175

Arg Ser Leu Pro Gly Cys Gln Glu Ile Ala Glu Glu Phe Arg Ala Gln
            180             185             190

Glu Ile Asp Gly Gln Ala Leu Leu Leu Leu Lys Glu Asp His Leu Met
            195             200             205

Ser Ala Met Asn Ile Lys Leu Gly Pro Ala Leu Lys Ile Tyr Ala Arg
    210             215             220

Ile Ser Met Leu Lys Asp Ser
225             230
```